United States Patent [19]

Nakao et al.

[11] Patent Number: 5,400,770
[45] Date of Patent: Mar. 28, 1995

[54] DEVICE UTILIZABLE WITH ENDOSCOPE AND RELATED METHOD

[76] Inventors: Naomi L. Nakao, 303 E. 57th St., New York, N.Y. 10022; Peter J. Wilk, 185 W. End Ave., New York, N.Y. 10023

[21] Appl. No.: 203,669

[22] Filed: Feb. 28, 1994

Related U.S. Application Data

[63] Continuation of Ser. No. 821,410, Jan. 15, 1992, abandoned.

[51] Int. Cl.$^6$ ............................................. A61B 1/00
[52] U.S. Cl. ............................................. 128/4; 604/96; 604/100; 604/101
[58] Field of Search .................. 604/96, 100, 101, 103, 604/163, 171, 172; 128/4, 10, 11

[56] References Cited

U.S. PATENT DOCUMENTS

| | | |
|---|---|---|
| 2,701,559 | 2/1955 | Cooper . |
| 3,483,859 | 12/1969 | Pittman . |
| 3,913,568 | 10/1975 | Carpenter ............................ 128/11 |
| 4,091,816 | 5/1978 | Elam ................................. 604/101 X |
| 4,141,364 | 2/1979 | Schultze ............................... 604/96 |
| 4,230,108 | 10/1980 | Young ............................... 604/101 X |
| 4,423,725 | 1/1984 | Baran et al. ....................... 604/101 X |
| 4,441,495 | 4/1984 | Hicswa . |
| 4,498,473 | 2/1985 | Gereg ................................ 604/96 X |
| 4,676,228 | 6/1987 | Krasner et al. .................... 604/101 X |
| 4,690,138 | 9/1987 | Heyden ............................. 604/100 X |
| 4,693,243 | 9/1987 | Buras . |
| 4,700,700 | 10/1987 | Eliachar ............................. 604/101 X |
| 4,737,142 | 4/1988 | Heckele . |
| 4,846,153 | 7/1989 | Berci ................................. 128/6 |
| 4,875,897 | 10/1989 | Lee . |
| 4,981,470 | 1/1991 | Bombeck, IV ................... 606/196 X |
| 5,025,778 | 6/1991 | Silverstein et al. . |
| 5,098,379 | 3/1992 | Conway et al. ................... 604/96 X |
| 5,112,310 | 5/1992 | Grobe ............................... 604/96 X |
| 5,188,596 | 2/1993 | Condon et al. ................... 128/6 X |

FOREIGN PATENT DOCUMENTS

| | | | |
|---|---|---|---|
| 2659440 | 7/1977 | Germany . | |
| 2185400 | 7/1987 | United Kingdom ............ | 128/6 |
| 9014858 | 12/1990 | WIPO ............................ | 128/4 |
| 9014859 | 12/1990 | WIPO ............................ | 128/4 |

*Primary Examiner*—Richard J. Apley
*Assistant Examiner*—Beverly A. Meindl
*Attorney, Agent, or Firm*—R. Neil Sudol; Henry D. Coleman

[57] ABSTRACT

A surgical device for use with an endoscope to perform gastroesophageal hemostasis operations on bleeding gastroesophageal varices and for forceful esophageal dilation to correct achalasia comprises an insertion member, an inflatable balloon, an attachment component in the form of a substantially thin-walled elongate tubular sheath made of a flexible material for removably attaching the balloon in a collapsed configuration to the endoscope insertion member, and an inflation device operatively connected to the balloon for enabling an expansion of the balloon from the collapsed configuration to an expanded configuration. The sheath is provided along its length and on an outer surface with a distance scale to enable the positioning or alignment of the balloon with the desired surgical site in cases where the endoscope protrudes from the distal end of the sheath and is therefore staggered by a predetermined distance with respect to the balloon. Alternatively or additionally, the balloon is transparent and at least a portion of the sheath in a region about the balloon is transparent. In this case, the distal end of the endoscope is preferably aligned with the balloon. Once the desired surgical site has been located visually through use of the endoscope, the distal end of the endoscope's insertion member being juxtaposed to the surgical site, the balloon is inflated.

14 Claims, 3 Drawing Sheets

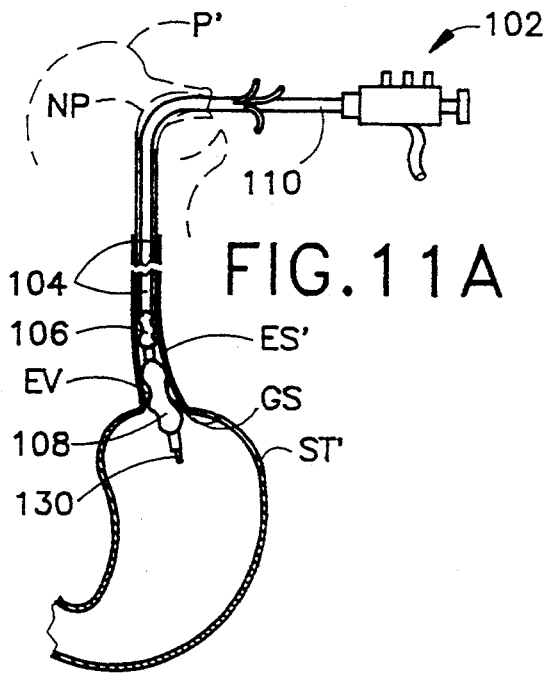
FIG. 11A
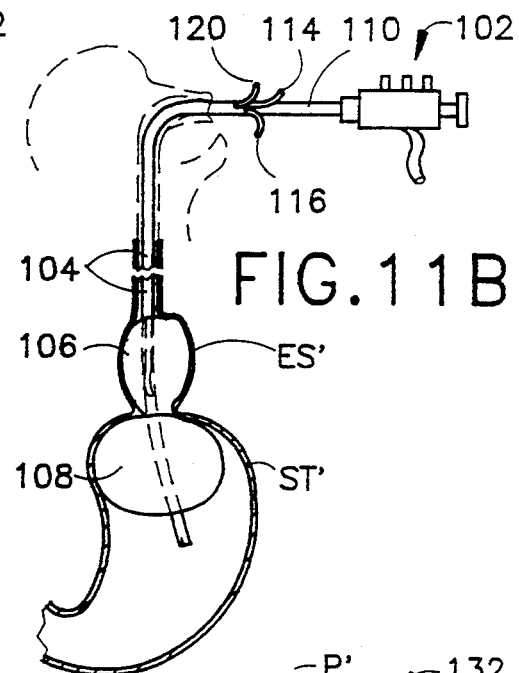
FIG. 11B
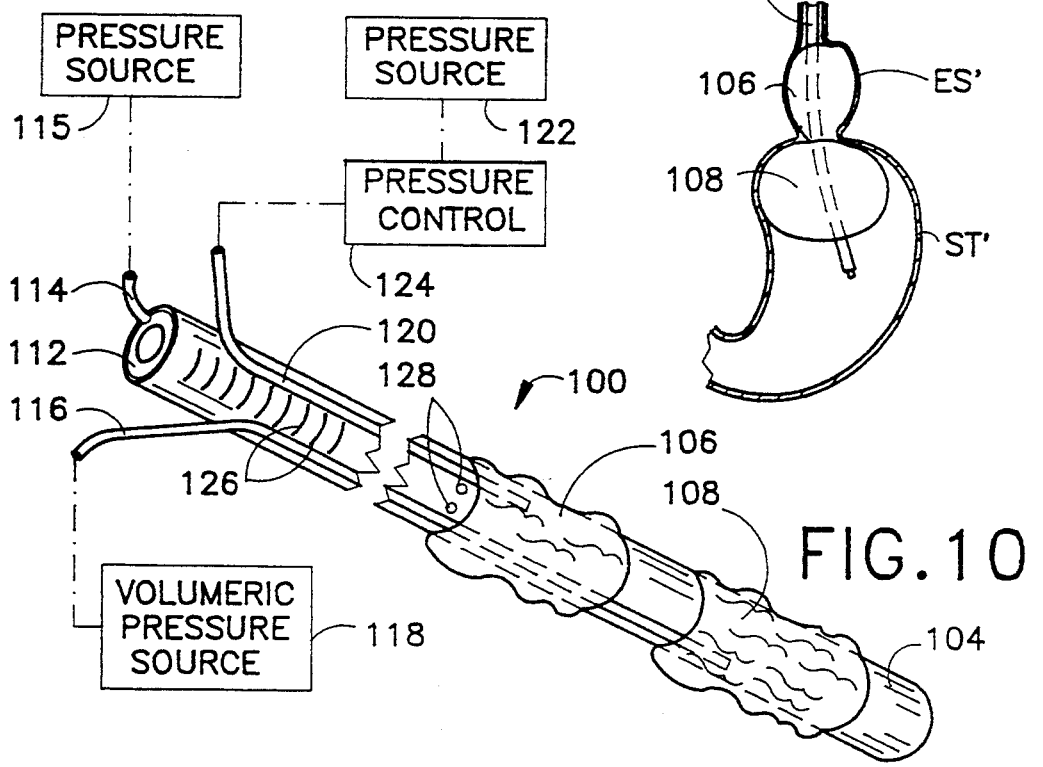
FIG. 11C
FIG. 10

DEVICE UTILIZABLE WITH ENDOSCOPE AND RELATED METHOD

This application is a continuation of application Ser. No. 07/821,410, filed Jan. 15, 1992, now abandoned.

BACKGROUND OF THE INVENTION

This invention relates to a device utilizable with an endoscope for performing surgical operations with the aid of the endoscope. This invention also relates to an associated surgical method. The device and the method are particularly efficacious in the treatment of achalasia. In a modified form, the invention is applicable to the treatment of bleeding varices, particularly gastric and/or esophageal varices.

Achalasia is a chronic motor disorder resulting from aperistalsis of the smooth muscle portion of the esophagus and leading to functional obstruction proximal to the lower esophageal sphincter. The pathogenesis involves degeneration of the nerve cells of Auerbach's plexis, which in turn leads to aperistalsis and incomplete relaxation of the lower esophageal sphincter. The clinical manifestations include dysphagia, i.e., difficulty in swallowing, for both liquids and solids.

One of the most effective treatments of achalasia is forceful pneumatic dilitation or dilation of the esophagus. This procedure entails the passage of a balloon into the esophagus under fluoroscopic guidance. Once the balloon is positioned at the gastroesophageal junction, the balloon is suddenly and forcefully inflated, thereby tearing muscle fibers. When done correctly, this procedure provides the patient with relief of the symptoms and results in improved swallowing.

The forceful pneumatic dilitation or dilation of the esophagus frequently results in complications due mainly to an incorrect placement of the balloon. Because the balloon is positioned under fluoroscopic guidance, visualization is sometimes inaccurate and the balloon is inflated at an improper location. Such error can cause perforations of the esophagus.

Another gastroesophageal disorder is bleeding varices. Gastric and esophageal varices are a devastating complication of portal hypertension. To treat such bleeding varices, it is necessary at times to use a long tube with two inflatable balloons at a distal end, known as a "Blakemore Tube." In using this device to stop the flow of blood in the stomach, the tube is blindly inserted into the esophagus until it is believed that the most distal of the two balloons is located in the patient's stomach. That balloon is then inflated and the tube placed in tension (e.g., via attachment to a weight outside of the patient) to pull the inflated balloon against the stomach wall at the gastroesophageal junction. In the event that bleeding esophageal varices are to be treated, the relatively proximal balloon is also inflated.

The rate of complications in the use of the Blakemore tube is immense. The complications result mainly from poor placement or slippage of the tube. In addition, the relatively proximal balloon sometimes erodes into the esophagus, causing bleeding, perforation and necrosis of the esophagus.

OBJECTS OF THE INVENTION

An object of the present invention is to provide a surgical device and an associated surgical technique which utilize an endoscope in treating disorders of the digestive tract.

A more particular object of the present invention is to provide such a surgical device and method whereby the incidence of complications in achalasia corrective surgery is reduced, if not eliminated.

A similar particular object of the present invention is to provide such a surgical device and method whereby complications arising in the treatment of bleeding gastroesophageal varices are reduced.

Another, even more particular, object of the present invention is to provide such a device and method which increase the accuracy with which an esophageal balloon is juxtaposed to esophageal tissues in the treatment of achalasia or bleeding esophageal varices.

A further particular object of the present invention is to provide such a device and method which facilitate the immediate inspection of the surgical site upon completion of the surgical operation.

Yet another particular object of the present invention is to provide a surgical instrument and an associated technique which decrease morbidity in operations to correct achalasia or to treat bleeding gastric and/or esophageal varices.

SUMMARY OF THE INVENTION

A surgical device for use with an endoscope having an insertion member insertable into a patient comprises, in accordance with the present invention, an inflatable balloon, an attachment component for removably attaching the balloon in a collapsed configuration to the endoscope insertion member, and an inflation device operatively connected to the balloon for enabling an expansion of the balloon from the collapsed configuration to an expanded configuration.

Pursuant to another feature of the present invention, the attachment component includes a substantially thin-walled elongate tubular sheath made of a flexible material. The sheath has a use configuration with an inner diameter larger than an outer diameter of the insertion member of the endoscope, whereby the sheath may be removably disposed about such insertion member to substantially surround the insertion member prior to insertion thereof into a patient.

Pursuant to another feature of the present invention, the sheath is provided with a securing element for facilitating attachment thereof to the insertion member of the endoscope and for concomitantly facilitating subsequent removal of the sheath from the insertion member of the endoscope. The securing element may take the form of at least one pair of cooperating zip-lock or snap-lock elements. The zip-lock or snap-lock elements may extend longitudinally along the sheath. Alternatively, the securing element includes an air-tight cylindrical inner tube incorporated into the sheath and means attached to the sheath for alternately inflating and deflating the inner tube.

Pursuant to another feature of the present invention, the sheath is provided along its length and on an outer surface with a series of distance markings, i.e., a distance scale. These markings enable the positioning or alignment of the balloon with the desired surgical site in cases where the endoscope protrudes from the distal end of the sheath and is therefore staggered by a predetermined distance with respect to the balloon.

Pursuant to an alternative feature of the present invention, the balloon is transparent and at least a portion of the sheath in a region about the balloon is transparent. In this case, the distal end of the endoscope is preferably aligned with the balloon. Once the desired surgical site has been located visually through use of the endoscope, the distal end of the endoscope's insertion member being juxtaposed to the surgical site, the balloon is inflated.

According to a specific feature of the present invention, the balloon is annular in configuration and surrounds a portion of the sheath.

In accordance with another feature of the present invention, an additional balloon is attached to the sheath and an additional inflation device is operatively connected to the additional balloon for enabling an expansion of the additional balloon from a collapsed configuration to an expanded configuration. This configuration is particularly useful for the hemostasis of bleeding gastroesophageal varices, one balloon being a gastric balloon and the other balloon being an esophageal balloon. As with the prior art Blakemore Tube, it is contemplated that the gastric balloon is inflated, whether gastric or esophageal varices are being treated. However, the esophageal balloon is inflated only for the treatment of esophageal varices.

A method for performing an endoscopic surgical operation comprises, in accordance with the present invention, the steps of (a) inserting into a patient an insertion member of an endoscope, the insertion member being provided with a balloon in a collapsed configuration, (b) using the endoscope to visually locate a surgical site within the patient, (c) upon the locating of the surgical site, manipulating the insertion member to juxtapose the balloon to the surgical site, and (d) inflating the balloon to contact the surgical site.

According to another feature of the present invention, the method further comprises the step of attaching the balloon in the collapsed configuration to the insertion member prior to the step of inserting. More particularly, the step of attaching the balloon to the endoscope insertion member includes the steps of (i) providing a tubular sheath with the balloon attached in the collapsed configuration to an outer surface of the sheath and (ii) disposing the sheath about the insertion member to enclose at least a distal end portion of the sheath.

According to a further feature of the present invention, the method further comprises the step of lubricating the endoscope insertion member prior to the disposition of the sheath about the insertion member. In that case, the sheath is slid about the endoscope insertion member. More specifically, the sheath includes an airtight cylindrical inner tube incorporated into the sheath and means attached to the sheath for alternately inflating and deflating the inner tube. The method then includes the additional step of inflating the inner tube upon disposition of the endoscope insertion member inside the sheath and prior to the insertion of the endoscope into the patient.

Pursuant to yet another feature of the present invention, the method comprises the additional steps of (i) deflating the inner tube upon the completed inflating of the balloon, (ii) sliding the insertion member relative to the sheath upon the deflating of the inner tube, and (iii) upon the sliding of the insertion member, using the endoscope to visually inspect the surgical site through the sheath and the balloon.

Where the method is used specifically for the hemostasis of bleeding varices, the balloon is one of a plurality of separately inflatable balloons attached to the sheath, including a gastric balloon for the hemostasis of bleeding gastric varices and an esophageal balloon for the hemostasis of bleeding esophageal varices. The sheath member is placed in tension upon inflation of the gastric balloon, and the endoscope insertion member is withdrawn from the sheath upon inflation of the gastric and/or esophageal balloon. The endoscope insertion member may be subsequently reinserted into the sheath to enable visual inspection of the surgical site.

According to a preferred feature of the present invention, particularly for the treatment of bleeding gastroesophageal varices, the sheath and the balloon are transparent. In that case the distal end of the endoscope insertion member is disposed proximally of a distal end of the sheath (i.e., inside the sheath and inwardly of the balloon). The endoscope's optical system then used to monitor internal tissues of the patient through the sheath and the balloon. This method may be used in the treatment of achalasia, bleeding gastroesophageal varices and other disorders of the digestive tract.

A surgical device utilizable with an endoscope specifically for the hemostasis of gastroesophageal varices comprises a substantially thin-walled elongate tubular sheath made of a flexible material, the sheath having a use configuration with an inner diameter larger than an outer diameter of an insertion member of the endoscope, whereby the sheath may be removably disposed about such insertion member to substantially surround same prior to insertion of the insertion member into a patient. A first inflatable balloon is attached in a collapsed configuration to a distal end of the sheath, while a second inflatable balloon attached in a collapsed configuration to a distal end of the sheath proximally of the first balloon. A first inflation device is operatively connected to the first balloon for enabling an expansion of the first balloon to an expanded configuration independently of the expansion state of the second balloon, and second inflation device is operatively connected to the second balloon for enabling an expansion of the second balloon to an expanded configuration independently of the expansion state of the first balloon.

Preferably, the sheath is provided with a securing device in the form of a cylindrical balloon or inner tube incorporated into the sheath along an inner side thereof and a device attached to the sheath for alternately inflating and deflating the inner tube. Also, the first balloon, the second balloon and at least a portion of the sheath in a region of the first balloon and the second balloon are transparent to enable monitoring of internal body tissues from inside the sheath via the endoscope's optical system.

A surgical device and an associated surgical technique in accordance with the present invention is particularly effective in the treatment of achalasia, bleeding gastroesophageal varices and similar disorders. In using a surgical device and method in accordance with the invention, the accuracy with which an esophageal dilator or a hemostasis balloon is positioned at the gastroesophageal sphincter is substantially increased, which reduces the incidence of complications in achalasia corrective surgery and the hemostatic treatment of bleeding gastroesophageal varices.

A surgical device and method in accordance with the present invention, when adapted for the hemostasis of bleeding gastroesophageal varices, is particularly effective because the endoscope may be removed and reinserted into the sheath, enabling periodic visual inspection of the varices to check for slippage and bleeding. In addition, the inflation state of the balloons may be continually monitored. Such periodic inspection may be undertaken by any attending physician. An endoscopist may be called if a problem requiring readjustment is detected.

A device and method in accordance with the present invention facilitate the immediate inspection of the surgical site upon completion of the surgery and decrease morbidity in operations to correct achalasia or to treat bleeding gastroesophageal varices.

BRIEF DESCRIPTION OF THE DRAWING

FIG. 10 is a schematic perspective view, on an enlarged scale, of a surgical device utilizable with an endoscope to apply hemostatic pressure to bleeding gastroesophageal varices, showing a pair of balloons in a deflated or collapsed configuration.

FIGS. 11A-11C are diagrams showing successive stages in an operation for applying hemostatic pressure to bleeding gastroesophageal varices, in accordance with the present invention.

DETAILED DESCRIPTION

Figure 1:
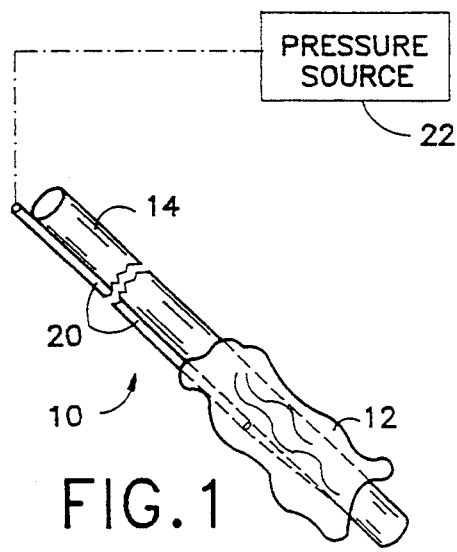
FIG. 1 is a schematic side perspective view of a device, in accordance with the present invention, for use with an endoscope for performing a gastroesophageal dilation, showing a balloon in a deflated or collapsed configuration.
Figure 3A:
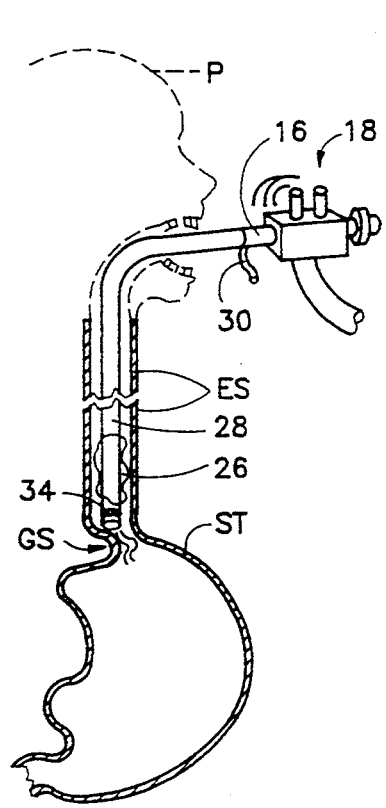
FIGS. 3A-3C are diagrams showing successive stages in a gastroesophageal dilation operation, in accordance with the present invention.

As illustrated in FIG. 1, a surgical device 10 for performing gastroesophageal dilation comprises an inflatable annular balloon 12 secured in a collapsed or deflated configuration to an outer surface of a flexible tubular sheath 14. Sheath 14 is a substantially thin-walled elongate member made of a flexible, biologically inert or non-toxic material such as polyethylene or rubber. Sheath 14 has a use configuration with an inner diameter larger than an outer diameter of an insertion member 16 of an endoscope 18 (see FIGS. 3A-3C), whereby the sheath may be removably disposed about insertion member 16 to substantially surround the insertion member prior to insertion thereof into a patient P (FIGS. 3A-3C).

Balloon 12 is fixed to a distal end of sheath 14. Sheath 14 serves as an attachment component for removably attaching balloon 12 in a collapsed configuration to endoscope insertion member 16.

Figure 3B:
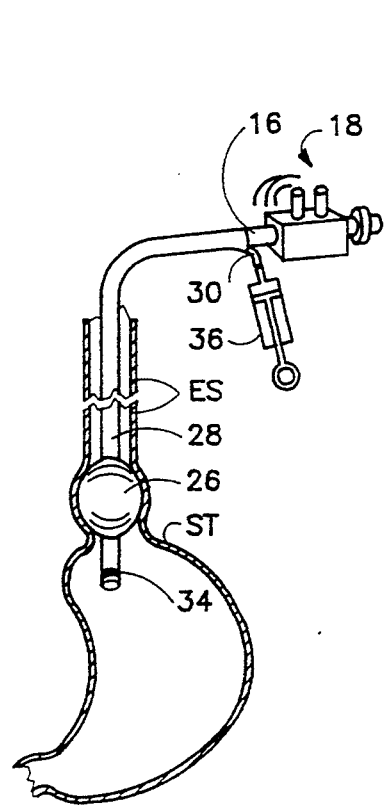
Figure 3C:
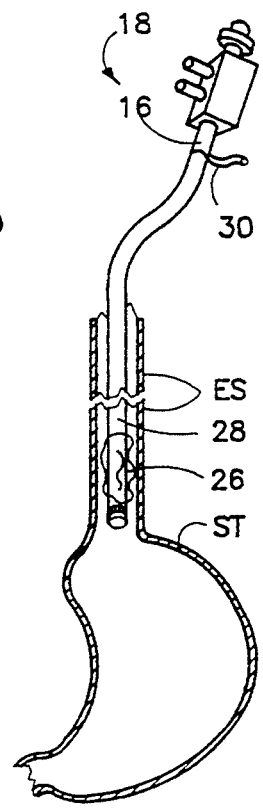
Figure 4:
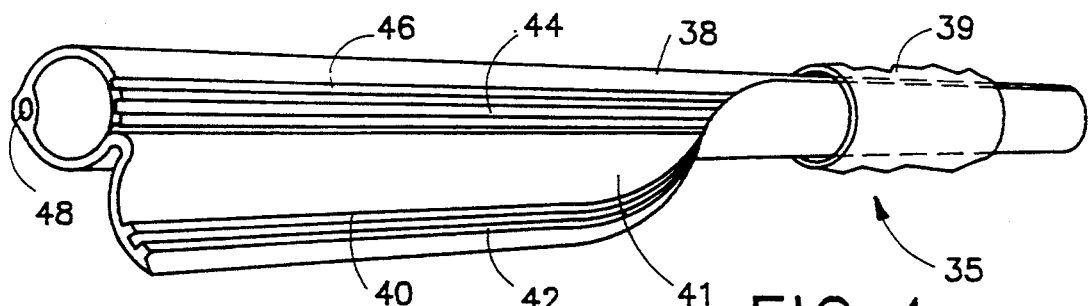
FIG. 4 is a perspective view of a further gastroesophageal dilation device for use with an endoscope, in accordance with the present invention.

Gastroesophageal dilation device 10 further comprises an inflation tube 20 extending longitudinally along sheath 14 and connected to balloon 12 for enabling a rapid and forceful expansion of the balloon from the collapsed configuration (FIG. 1) to an expanded configuration (see FIG. 3B).

Sheath 14 is provided with a securing element (not shown in FIG. 1) for facilitating attachment thereof to endoscope insertion member 16 and for concomitantly facilitating subsequent removal of the sheath from the endoscope insertion member. Such a securing element is described in detail hereinafter with reference to specific embodiments illustrated in FIGS. 4-9.

Balloon 12 is transparent and at least a portion of sheath 14 in a region about balloon 12 is also transparent. Accordingly, endoscope insertion member 16 may be positioned inside sheath 14 so that a distal end of the endoscope insertion member is aligned with or surrounded by balloon 12.

In using the gastroesophageal dilation device 10 of FIG. 1, endoscope insertion member 16 is inserted into tubular sheath 14 and is then inserted, with the sheath and balloon 12, into a patient's esophagus. The endoscope is then used to visually locate a constriction in the esophagus, for example, a gastroesophageal constriction characteristic of achalasia. In so using the endoscope, a visual image is obtained through the wall of sheath 14 and balloon 12. Once the constriction has been located visually, and the endoscope insertion member adjusted relative to the patient so that the balloon 12 at the distal end of the endoscope's insertion member is juxtaposed to the desired surgical site, balloon 12 is forcefully and suddenly inflated by pressurized air from a source 22 connected to inflation tube 20. Balloon 12 is then deflated and the dilation site is inspected by the endoscope through sheath 14 and balloon 12. If necessary, the procedure may be repeated. To repeat the operation, the original gastroesophageal dilation device 10 may be withdrawn (with the endoscope insertion member) and a new gastroesophageal dilation device may be attached to the endoscope insertion member 16.

Sheath 14 may be more rigid at its distal end than along the remainder of its length insofar as the endoscope insertion member does not extend to the distal end of the sheath and therefore does not support that portion of the sheath during an insertion of the endoscope and the gastroesophageal dilation device 10 into the patient.

Figure 2:
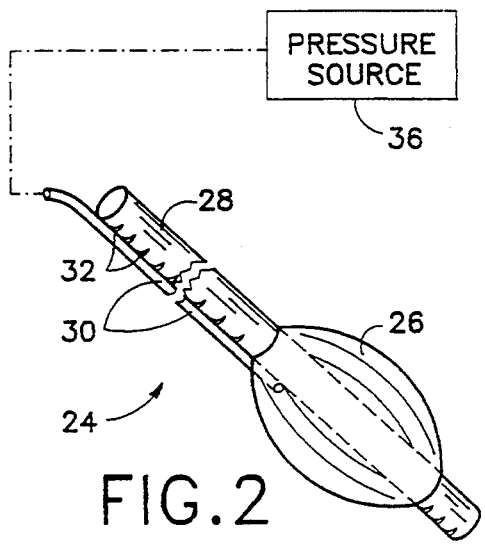
FIG. 2 is a schematic side perspective view of another device, in accordance with the present invention, for use with an endoscope for performing a gastroesophageal dilation, showing a balloon in an inflated or expanded configuration.

FIG. 2 depicts another gastroesophageal dilation device 24 comprising an inflatable annular balloon 26 secured in a collapsed or deflated configuration to an outer surface of a flexible tubular sheath 28. Sheath 28 is a substantially thin-walled elongate member made of a flexible, biologically inert or non-toxic material such as polyethylene or rubber. Sheath 28 has a use configuration with an inner diameter larger than an outer diameter of endoscope insertion member 16 (see FIGS. 3A-3C), whereby the sheath may be removably disposed about insertion member 16 to substantially surround the insertion member prior to insertion thereof into a patient.

Balloon 26 is fixed to a distal end of sheath 28. Sheath 28 serves as an attachment component for removably attaching balloon 26 in a collapsed configuration to endoscope insertion member 16.

Gastroesophageal dilation device 24 further comprises an inflation tube 30 extending longitudinally along sheath 28 and connected to balloon 26 for enabling a rapid and forceful expansion of the balloon from the collapsed configuration (FIG. 2) to an expanded configuration (see FIG. 3B).

Sheath 28 is provided with a securing element (not shown in FIG. 2) for facilitating attachment thereof to endoscope insertion member 16 and for concomitantly facilitating subsequent removal of the sheath from the endoscope insertion member. Such a securing element is described in detail hereinafter with reference to specific embodiments illustrated in FIGS. 4–9.

Sheath 28 is provided along its length (or at least along a proximal portion) and on an outer surface with a series of distance markings 32 preferably in the form of a metric scale. These markings enable the positioning or alignment of balloon 26 with respect to the desired surgical site, e.g., a gastroesophageal constriction.

FIGS. 3A–3C depict successive stages in the use of gastroesophageal dilation device 24. Prior to an operation proper, insertion member 16 of endoscope 18 is inserted into tubular sheath 28 so that a distal end portion 34 of insertion member 16 protrudes from a distal end of sheath 28. Insertion member 16 with sheath 28 and balloon 26 is inserted into the esophagus ES of patient P. Endoscope 18 is then used to visually locate a gastroesophageal constriction GS characteristic of achalasia, at the upper end of the patient's stomach ST. Upon the locating of constriction GS, the operating surgeon notes the particular distance marking 32 juxtaposed to a predetermined point on patient P (e.g., the patient's front teeth). To align or juxtapose balloon 26 to constriction GS, the surgeon then pushes endoscope insertion member 16, with sheath 28 and balloon 26 fixed thereto, a predetermined distance further into the patient's esophagus ES. This predetermined distance generally corresponds to the distance between the tip of endoscope insertion member 16 and balloon 26.

Upon the juxtaposition of balloon 26 to the desired surgical site, balloon 26 is forcefully and suddenly inflated by pressurized air from a source 36 (e.g., a syringe) connected to inflation tube 30. Balloon 26 is subsequently deflated and endoscope insertion member 16 pulled the predetermined distance back out of the patient's esophagus ES. Endoscope 18 is then used to inspect the surgical site. If necessary, the procedure may be repeated. To repeat the operation, the original gastroesophageal dilation device 24 may be withdrawn (with the endoscope insertion member) and a new gastroesophageal dilation device may be attached to the endoscope insertion member 16.

Figure 5:
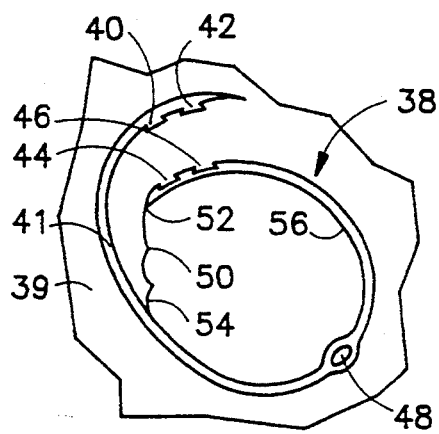
FIG. 5 is an end view of a dilation device of FIG. 4, showing a sheath member in an opened configuration.
Figure 6:
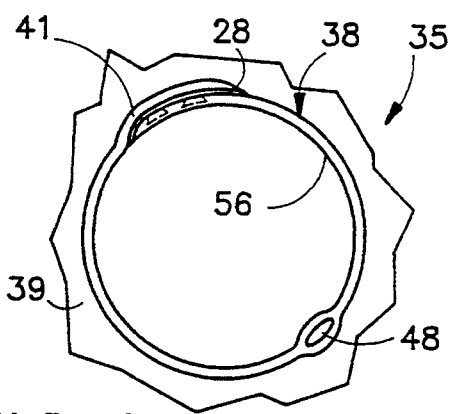
FIG. 6 is an end view of the sheath member of FIGS. 4 and 5, showing the sheath member in a closed, use, configuration.

As shown in FIGS. 4–7, another gastroesophageal dilation device 35 comprises a slotted sheath 38 provided at a distal end with an inflatable annular balloon 39. Sheath 38 is provided on an inner surface of a flap 41 with a pair of longitudinally extending ribs or beads 40 and 42 which cooperate with respective longitudinally extending grooves 44 and 46 on an outer surface of sheath 38 to close sheath 38 about an endoscope insertion member. Ribs 40 and 42 are pressed into grooves 44 and 46 by a pressure applied longitudinally from a distal end of sheath 38 to a proximal end thereof. This pressure may be applied manually with a simple hand contact or may be facilitated by the provision of a zipper mechanism (not illustrated). As illustrated in FIG. 6, sheath 38 has a substantially smooth external surface upon a closure stroke which presses ribs 40 and 42 into grooves 44 and 46. Balloon 39 is fitted about sheath 38 so that sheath 38 may be closed in the region of balloon 39 via manual pressure applied through the balloon.

Alternatively, sheath 38 may be continuously cylindrical (unslotted) in the area of balloon 39. In that event, ribs 40 and 42 and grooves 44 and 46 extend only to balloon 39. The distal end of sheath 38 may be provided with supplementary snap-lock or other closure elements (not illustrated) to fasten the distal end of sheath 38 to endoscope insertion member 16 (FIGS. 3A–3C).

Zip-lock ribs 40 and 42 and grooves 44 and 46 serve to facilitate attachment or securement of sheath 38 to an endoscope insertion member (optionally in a fluid tight seal) prior to an endoscopic surgical operation and to concomitantly facilitate subsequent removal of the sheath from the insertion member of the endoscope after the termination of the operation.

Sheath 38 is provided internally with at least one longitudinally extending channel 48 which communicates with balloon 39, whereby the balloon may be forcefully and suddenly inflated as described herein to enlarge a gastroesophageal constriction.

Sheath 38 is made of a strong, flexible and substantially elastic material such as polyethylene or rubber.

As shown in FIGS. 5 and 6, sheath 38 may be provided with an internal membrane 50 extending longitudinally the length of the sheath. Membrane 50 is secured along its longitudinal edges 52 and 54 to an inner surface 56 of sheath 38.

Figure 8:
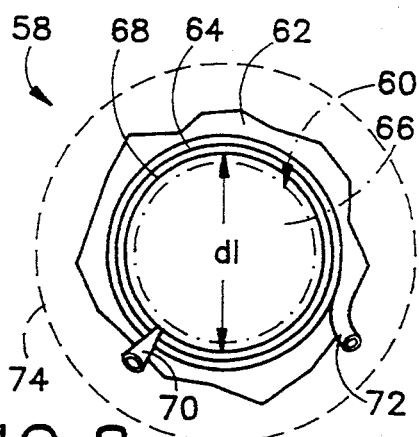
FIG. 8 is a schematic end view of an additional gastroesophageal dilation device in accordance with the present invention.
Figure 7:
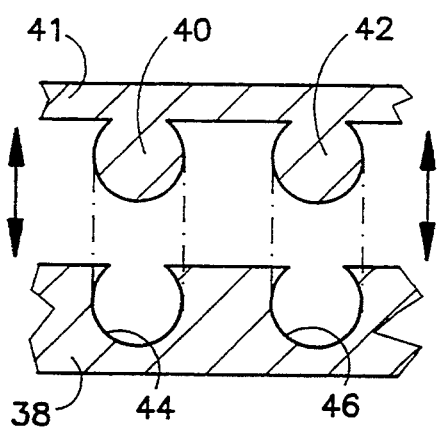
FIG. 7 is a partial cross-sectional view taken transversely to a longitudinal axis of the sheath of FIG. 4.

As shown in FIG. 8, another gastroesophageal dilation device 58 for use with an endoscope 60 comprises an inflatable annular balloon 62 secured in a collapsed or deflated configuration to an outer surface of a flexible tubular sheath 64. Sheath 64 is a substantially thin-walled elongate member made of a flexible, biologically inert or non-toxic material such as polyethylene or rubber.

Sheath 64 has a use configuration with an inner diameter d1 larger than an outer diameter of an insertion member 66 of endoscope 60, whereby the sheath may be removably disposed about insertion member 66 to substantially surround the insertion member prior to insertion thereof into a patient. Inner diameter d1 is defined by an inflated or expanded configuration of a cylindrical balloon member or inner tube 68 attached to or integral with sheath 64 along an inner surface thereof.

Balloon member 68 is in a collapsed or deflated configuration initially, i.e., prior to the commencement of a gastroesophageal dilation operation. Balloon 68 is provided at a proximal end of sheath 64 with an inlet 70 for enabling inflation of balloon 68 after insertion therethrough of endoscope insertion member 66. In an inflated configuration, balloon member 68 serves to securely attach sheath 64 to endoscope insertion member 66.

As further illustrated in FIG. 8, gastroesophageal dilation device 58 further comprises an inflation tube 72 extending longitudinally along sheath 64 and connected to outer balloon 62 for enabling a rapid and forceful expansion of that balloon from the collapsed configuration to an expanded configuration 74 upon a connection of tube 72 to a source of pressurized air (not illustrated).

Sheath 64 may be provided along an outer surface with longitudinally spaced distance markings (e.g., a metric scale, not illustrated) for enabling a positioning of outer balloon 62 at a gastroesophageal constriction pursuant to the method described hereinabove with reference to FIGS. 2 and 3A–3C. Alternatively or additionally, outer balloon 62, inner balloon 68, and at least a portion of sheath 64 in the neighborhood of balloon 62 are transparent, whereby balloon 62 may be positioned next to a gastroesophageal constriction in accordance with the procedure discussed above with reference to FIG. 1.

It is to be noted that all of the gastroesophageal dilation devices described herein are disposable. In the case of transparent components, the distal end of the sheath may be closed at a distal end. Such a closure facilitates sealing of the endoscope insertion member and thereby promotes sterility.

Figure 9:
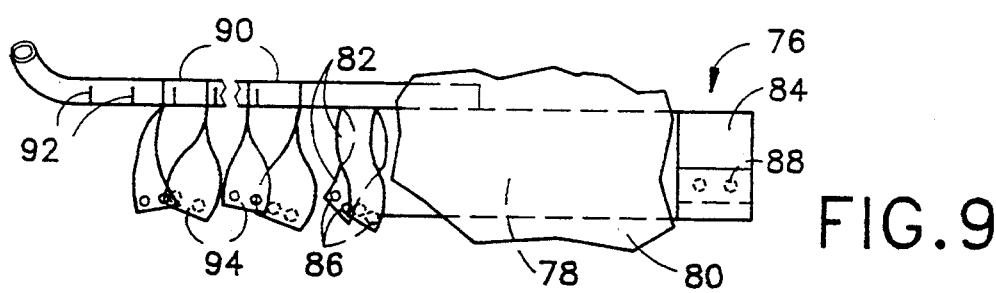
FIG. 9 is a schematic side elevational view of yet another gastroesophageal dilation device in accordance with the present invention.

FIG. 9 shows yet another gastroesophageal dilation device 76 including a shortened tubular sheath or sleeve 78. An inflatable annular balloon 80 is attached in a collapsed configuration to an outer surface of sleeve 78. Sleeve 78 is provided at opposite ends with a pair of strips 82 and 84 each provided with snap-lock or ziplock or other closure elements 86 and 88, whereby sleeve 78 together with balloon 80 may be attached to the distal end of an endoscope insertion member (not shown in FIG. 9). An elongate tube 90 is connected at a distal end to sleeve 78 and communicates at that end with balloon 80 for introducing pressurized air into the balloon during a gastroesophageal dilation operation.

Tube 90 may be provided with a series of equispaced distance markings 92, for example, a metric scale. In that event, the distal end of an endoscope insertion member protrudes from a distal end of sleeve 78 during utilization of the gastroesophageal dilation device 76 pursuant to the method of FIGS. 3A–3C. Tube 90 may be held in tension at a proximal end. Alternatively, tube 90 may be provided with a plurality of spaced connector strips 94 for attaching the tube to an endoscope insertion member at spaced locations therealong.

As discussed hereinabove, for example, with reference to FIG. 1, sleeve 78 and balloon 80 may be at least partially transparent for enabling positioning of the balloon at a gastroesophageal constriction by visually inspecting the constriction with an endoscope having an insertion member with a distal tip disposed inside sleeve 78.

As illustrated in FIG. 10, a device 100 utilizable with an endoscope 102 (FIGS. 11A and 11B) for applying hemostatic pressure to bleeding gastroesophageal varices comprises an elongate tubular sheath 104 generally made of a tough flexible material such as polyethylene. Attached to a distal end of sheath 104, on an outer surface thereof, is a relatively proximal esophageal balloon 106 and a relatively distal gastric balloon 108. Balloons 106 and 108 are in a collapsed or deflated state initially, i.e., prior to the insertion of an endoscope insertion member 110 (FIGS. 11A and 11B) into sheath 104 and prior to the commencement of an endoscopic procedure for the hemostatic treatment of bleeding gastroesophageal varices.

As discussed hereinabove with reference to FIG. 8, a cylindrical balloon or inner tube 112 is attached to or integral with sheath 104 along an inner surface thereof. Inner tube 112 is provided at a proximal end of sheath 104 with an inlet or connector 114 for coupling inner tube 112 to a pressure source 115 after an insertion of endoscope insertion member 110 through sheath 104. In an inflated configuration, inner tube 112 serves to securely attach sheath 104 to endoscope insertion member 110.

As illustrated in FIG. 10, gastroesophageal hemostasis device 100 further comprises a first inflation tube 116 extending longitudinally along sheath 104 and connected to gastric balloon 108 for enabling an expansion of that balloon from the collapsed configuration to an expanded configuration upon a connection of tube 116 to a volumetric pressure source 118. Pressure source 118 is designed to inflate gastric balloon 108 to a predetermined volume.

Gastroesophageal hemostasis device 100 also comprises a second inflation tube 120 extending longitudinally along sheath 104 and connected to esophageal balloon 106 for enabling a dilation of that balloon from the collapsed configuration to an expanded configuration upon a connection of tube 120 to a pressure source 122. Pressure source 122 is preferentially connected to a pressure control unit 124 designed to inflate esophageal balloon 106 to a predetermined pressure. Pressure control unit may take the simple form of a pressure gauge which is periodically monitored by hospital personnel to ascertain that the esophageal balloon 106 is maintained at a predetermined pressure level.

Sheath 104 may be provided along an outer surface with longitudinally spaced distance markings 126 (e.g., a metric scale) for enabling a positioning of balloons 106 and 108 at a desired gastroesophageal location pursuant to the method described hereinabove with reference to FIGS. 2 and 3A–3C. Preferably, however, balloons 106 and 108, inner tube 112, and at least a portion of sheath 104 in the neighborhood of balloons 106 and 108 are transparent, whereby balloons 106 and 108 may be positioned at bleeding gastroesophageal varices in accordance with the procedure discussed below with reference to FIGS. 11A–11C.

Gastroesophageal hemostasis device 100 is provided proximally of esophageal balloon 106 with a plurality of apertures or canals 128 extending through sheath 104 and inner tube 112, whereby accumulating saliva may drain from the esophagus ES' (FIGS. 11A–11C) into the stomach ST' of a patient P'.

Prior to a gastroesophageal hemostasis operation, insertion member 110 of endoscope 102 is lubricated and inserted into sheath 104. Pressure source 115 is then connected and actuated to inflate inner tube 112. Subsequently, insertion member 110 with sheath 104 firmly attached is inserted into the the patient's esophagus ES', for example, through a nasal passage NP.

A distal tip 130 of insertion member 110 may protrude initially from the distal end of sheath 104. The endoscope is used, upon the positioning of insertion member 110 and sheath 104 inside esophagus ES' and the upper end of stomach ST', to visually locate and inspect gastric varices GV and esophageal varices EV for bleeding.

Upon a locating of bleeding gastric varices GS, volumetric pressure source 118 (FIG. 10) is operated to inflate gastric balloon 108 to a predetermined volume, as shown in FIGS. 11B and 11C. At this juncture, sheath 104 may be connected to a weight or tension applying device 132, to forcibly bring balloon 108 into contact with gastric varices GV.

If esophageal varices EV are bleeding, as determined upon visual inspection via endoscope 102, pressure sources 118 and 122 are operated to inflate both balloons 108 and 106. Tension is applied to sheath 104 to bring gastric balloon 108 into forceful engagement with the lining of stomach ST'.

Upon the inflation of balloons 106 and 108, pressure source 115 is deactivated or disconnected to allow deflation of inner tube 112. Endoscope insertion member 110 may then be partially withdrawn, as illustrated in FIG. 11B, to enable a visual inspection of gastric varices GV and esophageal varices EV through sheath 104 and balloons 108 and 106, respectively.

If the placement of balloons 106 and 108 is inaccurate, inner tube 112 is again inflated, the tension application device 132 (FIG. 11C) released, and balloons 106 deflated. The procedure is then repeated to properly position balloons 106 and 108.

Upon the successful placement of balloons 106 and 108, inner tube 112 is deflated and endoscope insertion member 110 withdrawn from sheath 104, as illustrated in FIG. 11C. The endoscope insertion member 110 may be subsequently reinserted into sheath 104 for a visual inspection of varices GV and EV to check for slippage and bleeding. In addition, the inflation state of balloons 106 and 108 may be monitored.

It is to be noted that inflation tubes 116 and 120 may be incorporated into sheath 104 (compare channel 48 in FIGS. 4-6), rather than attached as separate elements to an outer surface of the sheath. Also, inner tube 112 may be optionally inflated subsequent to the withdrawal of endoscope insertion member 110, to provide increased support to balloons 106 and 108.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proferred by way of example to facilitate comprehension of the invention and should not be construed to limit the scope thereof.

What is claimed is:

1. A method for performing an endoscopic surgical operation, comprising the steps of:
    providing an endoscope with an insertion member slidably inserted into a sheath, said sheath being provided at a distal end with an inflatable balloon attached in a collapsed configuration to an outer surface of said sheath, said sheath including an air-tight cylindrical inner tube incorporated into said sheath and means attached to said sheath for alternately inflating and deflating said inner tube;
    lubricating said insertion member;
    sliding said sheath about said insertion member to enclose at least a distal end portion of said insertion member;
    inflating said inner tube upon completion of said step of sliding;
    upon inflation of said inner tube, inserting, into an esophagus of a patient, said insertion member of said endoscope together with said sheath and said balloon in said collapsed configuration;
    using said endoscope to visually locate a bleeding surgical site within the esophagus of the patient;
    upon the locating of said surgical site, manipulating said insertion member to juxtapose said balloon to said surgical site;
    inflating said balloon to contact said surgical site and to thereby stop the bleeding at said surgical site;
    removing said insertion member from said sheath subsequently to said step of inflating, while maintaining said balloon in an inflated configuration at said surgical site; and
    upon inflation of said balloon, maintaining a tensile force on said sheath from a proximal end thereof, thereby holding said balloon in a desired position.

2. The method defined in claim 1, further comprising the steps of:
    deflating said inner tube upon the completed inflating of said balloon;
    sliding said insertion member relative to said sheath upon the deflating of said inner tube; and
    upon the sliding of said insertion member, using said endoscope to visually inspect said surgical site through said sheath and said balloon.

3. The method defined in claim 1 wherein a distal end of said insertion member is located distally of a distal end of said sheath, further comprising the steps of:
    monitoring distance markings on said sheath to determine depth of penetration of said insertion member when said surgical site is located by use of said endoscope; and
    adjusting penetration of said insertion member to align said balloon with said surgical site.

4. The method defined in claim 1 wherein said sheath and said balloon are transparent, a distal end of said insertion member being disposed proximally of a distal end of said sheath, step of using comprising the step of monitoring internal tissues of the patient through said sheath and said balloon.

5. The method defined in claim 1, further comprising the step of withdrawing said insertion member from the patient while maintaining said balloon inside the patient, whereby said step of removing is executed simultaneously with said step of withdrawing.

6. The method defined in claim 1, further comprising the step of withdrawing said insertion member from the patient, said step of removing being executed subsequently to said step of withdrawing.

7. A method for performing an endospcopic surgical operation, comprising the steps of:
    providing an endoscope with an insertion member slidably inserted into a sheath to a distal end portion of said sheath, said sheath being provided at a distal end with an inflatable balloon attached in a collapsed configuration to an outer surface of said sheath, said balloon being made of transparent material, said sheath being made of transparent material at least in a region of said balloon, said sheath including an air-tight cylindrical inner tube incorporated into said sheath and means attached to said sheath for alternately inflating and deflating said inner tube;
    inflating said inner tube;
    upon inflation of said inner tube, inserting, into a patient, said insertion member of said endoscope together with said sheath and said balloon in said collapsed configuration;
    using said endoscope to visually locate a surgical site within the patient;
    upon the locating of said surgical site, manipulating said insertion member to juxtapose said balloon to said surgical site;
    inflating said balloon to contact said surgical site;
    upon inflating said balloon, sliding said insertion member relative to said sheath while maintaining said sheath fixed relative to the patient;
    upon sliding of said insertion member relative to said sheath, inspecting said surgical site with said endoscope through said sheath and said balloon; and
    upon inflation of said balloon, maintaining a tensile force on said sheath from a proximal end thereof, thereby holding said balloon in a desired position.

8. The method defined in claim 7 wherein a distal end of said insertion member is located distally of a distal end of said sheath, further comprising the steps of:

monitoring distance markings on said sheath to determine depth of penetration of said insertion member when said surgical site is located by use of said endoscope; and adjusting penetration of said insertion member to align said balloon with said surgical site.

9. A method for performing an endoscopic surgical operation, comprising the steps of:

providing an endoscope with an insertion member slidably inserted into a sheath to a distal end portion of said sheath, said sheath being provided at a distal end with an inflatable balloon attached in a collapsed configuration to an outer surface of said sheath, said sheath including an air-tight cylindrical inner tube incorporated into said sheath and means attached to said sheath for alternately inflating and deflating said inner tube;

inflating said inner tube;

upon inflation of said inner rube, inserting, into an esophagus of a patient, said insertion member of said endoscope together with said sheath and balloon in said collapsed configuration;

using said endoscope to visually inspect the esophagus and the stomach of the patient;

manipulating said insertion member to insert said balloon into the stomach of the patient;

inflating said balloon in the stomach of the patient;

upon inflating said balloon, removing said insertion member from said sheath while maintaining the inflated balloon in the stomach of the patient; and also upon inflating said balloon, placing a tensile force on said sheath from a proximal end thereof to pull the inflated balloon against a stomach wall at said junction.

10. A method for performing an endoscopic surgical operation, comprising the steps of:

providing an endoscope with an insertion member;

providing a sheath having an air-tight cylindrical inner tube incorporated into said sheath in a deflated configuration, said sheath further including an inflatable balloon in a collapsed configuration at a distal end and along an outer surface of said sheath;

sliding said sheath about said insertion member to enclose at least a distal end portion of said sheath;

inflating said inner tube to an expanded configuration to lock said sheath to said insertion member upon completion of said step of sliding;

upon inflation of said inner tube to said expanded configuration, inserting, into a patient, said insertion member of said endoscope together with said inner tube in said expanded configuration;

using said endoscope to visually inspect internal tissues of the patient;

upon the locating of an desirable site via use of said endoscope, inflating said balloon in the patient;

upon inflation of said balloon, deflating said inner tube;

upon deflation of said inner tube, removing said insertion member from said sheath; and upon inflation of said balloon, pulling said sheath from a proximal end thereof.

11. The method defined in claim 10, further comprising the step of lubricating said insertion member prior to said step of sliding.

12. The method defined in claim 10 wherein said sheath is provided with distance markings, further comprising the step of monitoring said distance markings on said sheath to determine depth of penetration of said insertion member.

13. The method defined in claim 10 wherein said sheath and said balloon are at least partially transparent, further comprising the step of monitoring internal tissues of the patient through said sheath and said balloon upon deflation of said inner tube and prior to complete removal of said insertion member from said sheath.

14. A method for performing an endoscopic surgical operation, comprising the steps of:

providing an endoscope with an insertion member;

providing a sheath having an air-tight cylindrical inner tube incorporated into said sheath in a deflated configuration, said sheath further including an inflatable balloon in a collapsed configuration at a distal end and along an outer surface of said sheath;

sliding said sheath about said insertion member to enclose at least a distal end portion of said sheath;

inflating said inner tube to an expanded configuration to lock said sheath to said insertion member upon completion of said step of sliding;

upon inflation of said inner tube to said expanded configuration, inserting, into a patient, said insertion member of said endoscope together with said inner tube in said expanded configuration;

using said endoscope to visually inspect internal tissues of the patient;

upon the locating of an desirable site via use of said endoscope, inflating said balloon in the patient;

upon inflation of said balloon, deflating said inner tube;

upon deflation of said inner tube, removing said insertion member from said sheath; and maintaining said sheath partially in the esophagus of the patient with said balloon in an inflated configuration upon removal of said insertion member from said sheath.

* * * * *

UNITED STATES PATENT AND TRADEMARK OFFICE
CERTIFICATE OF CORRECTION

PATENT NO.   :   5,400,770
DATED        :   March 28, 1995
INVENTOR(S)  :   Naomi L. Nakao and Peter J. Wilk It is certified that error appears in the above-indentified patent and that said Letters Patent is hereby corrected as shown below:

Column 12, line 35, claim 7, change "endospcopic" to --endoscopic--.

Column 13, line 22, claim 9, change "rube" to --tube--.

Signed and Sealed this

Twenty-ninth Day of August, 1995

*Attest:*

BRUCE LEHMAN

*Attesting Officer*    *Commissioner of Patents and Trademarks*